United States Patent
Hwang et al.

(10) Patent No.: US 10,017,454 B2
(45) Date of Patent: Jul. 10, 2018

(54) METHOD OF MANUFACTURING BHCD AND DERIVATIVES THEREOF

(71) Applicant: Far Eastern New Century Corporation, Taipei (TW)

(72) Inventors: Der-Ren Hwang, Taoyuan (TW); Cheng-Ting Wang, Taoyuan (TW); Hsiao-Chan Wang, Taoyuan (TW); Chun-Chieh Chien, Taoyuan (TW); Kang-Rui Liu, Taoyuan (TW)

(73) Assignee: FAR EASTERN NEW CENTURY CORPORATION, Taipei (TW)

( * ) Notice: Subject to any disclaimer, the term of this patent is extended or adjusted under 35 U.S.C. 154(b) by 0 days.

(21) Appl. No.: 15/282,507

(22) Filed: Sep. 30, 2016

(65) Prior Publication Data
US 2017/0342016 A1 Nov. 30, 2017

(30) Foreign Application Priority Data

May 24, 2016 (TW) .............................. 105116133 A
Sep. 6, 2016 (TW) .............................. 105128821 A

(51) Int. Cl.
C07C 69/74 (2006.01)
C07C 67/303 (2006.01)

(52) U.S. Cl.
CPC ........ *C07C 67/303* (2013.01); *C07C 2101/14* (2013.01)

(58) Field of Classification Search
CPC ................................................ C07C 67/303
USPC .......................................................... 560/127
See application file for complete search history.

(56) References Cited

U.S. PATENT DOCUMENTS

| 6,762,276 B2 | 7/2004 | Sumner, Jr. et al. |
| 7,208,545 B1 * | 4/2007 | Brunner ................ C07C 67/303 524/569 |
| 9,127,136 B1 | 9/2015 | Bell et al. |
| 2015/0344622 A1 | 12/2015 | Mukerjee et al. |

FOREIGN PATENT DOCUMENTS

| CN | 1639225 A | 7/2005 |
| CN | 104003840 A | 8/2014 |

* cited by examiner

*Primary Examiner* — Deborah D Carr
(74) *Attorney, Agent, or Firm* — McClure, Qualey & Rodack, LLP

(57) ABSTRACT

The present disclosure provides a method of manufacturing bis(2-hydroxyethyl) cyclohexane-1,4-dicarboxylate (BHCD) and derivatives thereof. The method includes the following steps. A first reactant including bis-hydroxyethyl terephthalate (BHET) is provided. 2-(2-hydroxyethoxy) ethyl 2-hydroxyethyl terephthalate (BHEET) is added to the first reactant including BHET to form a second reactant. The second reactant is hydrogenated.

17 Claims, 1 Drawing Sheet

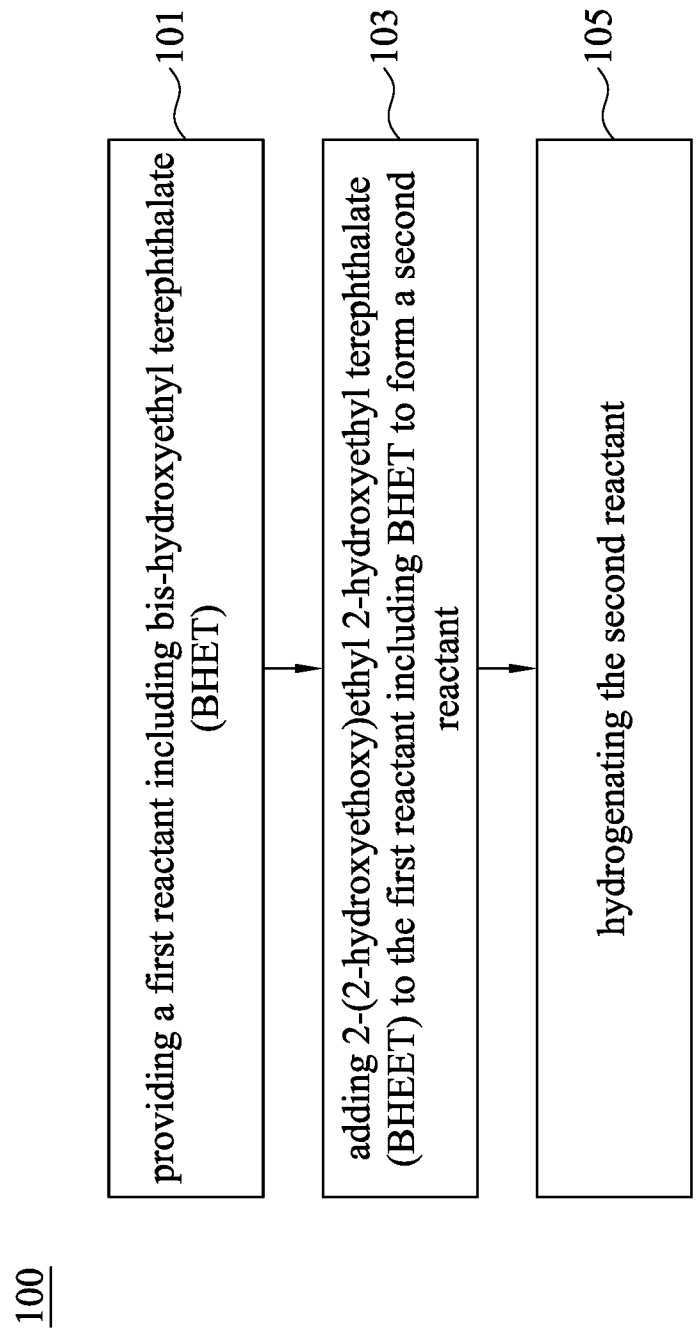

METHOD OF MANUFACTURING BHCD AND DERIVATIVES THEREOF

REFERENCE TO RELATED APPLICATION

This application claims priority to Taiwanese Application Serial Number 105116133, filed May 24, 2016, and Taiwanese Application Serial Number 105128821, filed Sep. 6, 2016, which are herein incorporated by reference.

BACKGROUND OF THE INVENTION

Field of the Invention

The present invention relates to a hydrogenation method of benzene derivatives, and in particular to a method for hydrogenating bis-hydroxyethyl terephthalate (BHET) to form bis(2-hydroxyethyl) cyclohexane-1,4-dicarboxylate (BHCD).

The Prior Art

Polyethylene terephthalate (PET) is a common polymer in our usual life. Because of its advantages such as good toughness, light weight and resistance of acid and alkali, PET becomes common containers of soft drinks, juices and carbonated drinks in recent years. Due to the increase of the needs, the production of PET product is increased thereby. A large amount of waste would be generated because the PET products are usually expendable for once.

Since PET having a strong chemical inertness can not be degraded by microbes in a short period of time, PET usually becomes a resource of the pollution in the ecological environment. Accordingly, the way that PET can be effectively recycled to produce a product having economic values and then solve the environmental pollution become an important issue. Accordingly, how effectively recycling PET to produce a product having economic value and then solve the environmental pollution become an important issue.

Patent CN104003840A discloses a method of hydrogenating a monomer, bis-hydroxyethyl terephthalate (BHET), derived by the degradation of waste PET. The BHET monomer is purified, and the purity of the BHET monomer is more than 99%. The method including the following step. BHET monomer is catalyzed by a Pd/C catalyst and reacted at a reaction pressure of 1.5-7.0 Mpa (equivalent to 217-1015 psi), a reaction temperature of 120-300° C. for 0.5-6.0 hours to form bis(2-hydroxyethyl) cyclohexane-1,4-dicarboxylate (BHCD). The disadvantage of the technique is that in addition to BHET monomer, the product derived by the degradation of waste PET usually has 10-30% dimer. Therefore, the purified step in this patent is necessary to get a good hydrogenation conversion rate.

U.S. Pat. No. 6,762,276B2 discloses a method of hydrogenating polyester oligomers containing terephthalic acid residues. The method discloses that a polyester oligomer including terephthalic acid residues is contacted with hydrogen in the presence of a supported or suspended hydrogenation catalyst under a hydrogen pressure of at least about 60 bars gauge (barg; about 870 pounds per square inch gauge—psig) and a temperature of about 180 to 280° C., so that the terephthalic acid residues are converted to 1,4-cyclohexanedicarboxylic acid residues. Compare with above patent, the purified step is not necessary, but only 10-50% terephthalic acid residues can be converted to 1,4-cyclohexanedicarboxylic acid residues in this method.

In summary, the prior art still has following problems. The BHET monomer has to be used as a reactant in the methods disclosed by prior art. If 1,4-cyclohexanedicarboxylic acid residues are derived by the hydrogenation conversion of terephthalic acid residues in the oligomer, instead of using the BHET monomer as a reactant, its hydrogenation conversion rate would be lower. Besides, the BHET monomer almost can not be hydrogenated under a lower temperature (<120° C.) and a solvent-free condition in the conventional method.

SUMMARY OF THE INVENTION

The first step of conventional chemical recycling of PET is that PET is degraded to form a first reactant including bis-hydroxyethyl terephthalate (BHET). The first reactant includes BHET monomer, BHET dimer and BHET oligomer. According to conventional technique, the first reactant has to be purified to obtain BHET monomer. Furthermore, the bis(2-hydroxyethyl) cyclohexane-1,4-dicarboxylate (BHCD) may be derived by subsequent hydrogenation at a high temperature (>120° C.) in the absence of solvent. Therefore, the process is complicated and high energy consumption.

In view of the issue met in the art, the present disclosure provides a method of manufacturing bis(2-hydroxyethyl) cyclohexane-1,4-dicarboxylate (BHCD) and derivatives thereof. According to the method of the present disclosure, a first reactant derived from PET degradation can be directly hydrogenated to obtain BHCD and the derivatives thereof without purification.

The present disclosure provides a method of manufacturing bis(2-hydroxyethyl) cyclohexane-1,4-dicarboxylate (BHCD) and derivatives thereof. The method includes the following steps. A first reactant including bis-hydroxyethyl terephthalate (BHET) is provided. 2-(2-hydroxyethoxy) ethyl 2-hydroxyethyl terephthalate (BHEET) is added to the first reactant including BHET to form a second reactant. The second reactant is hydrogenated.

In various embodiments of the present disclosure, the BHET in the first reactant is existed as a monomer, dimer, oligomer or a combination thereof.

In various embodiments of the present disclosure, the first reactant includes BHET monomer and BHET dimer.

In various embodiments of the present disclosure, the BHET dimer is 0-100 parts by weight based on 100 parts by weight of the BHET monomer in the first reactant.

In various embodiments of the present disclosure, the BHET dimer is 0-80 parts by weight based on 100 parts by weight of the BHET monomer in the first reactant.

In various embodiments of the present disclosure, the BHET dimer is 0-60 parts by weight based on 100 parts by weight of the BHET monomer in the first reactant.

In various embodiments of the present disclosure, the BHET oligomer has a structure represented by formula (1):

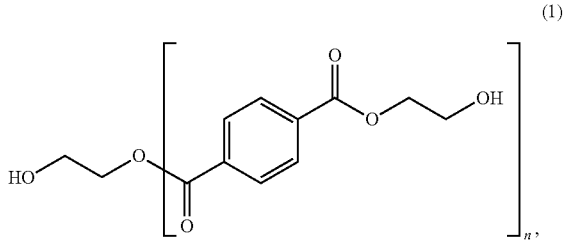

in which n is an integer of 3 to 10.

In various embodiments of the present disclosure, hydrogenating the second reactant is under a solvent-free condition.

In various embodiments of the present disclosure, hydrogenating the second reactant is at a temperature in a range of 80° C.–115° C.

In various embodiments of the present disclosure, hydrogenating the second reactant is at a temperature in a range of 85° C.–110° C.

In various embodiments of the present disclosure, the BHEET is 0.5-100 parts by weight based on 100 parts by weight of the BHET monomer in the second reactant.

In various embodiments of the present disclosure, the BHEET is 7-60 parts by weight based on 100 parts by weight of the BHET monomer in the second reactant.

In various embodiments of the present disclosure, the BHEET is 25-50 parts by weight based on 100 parts by weight of the BHET monomer in the second reactant.

In various embodiments of the present disclosure, the method further includes adding a catalyst to the second reactant before hydrogenating the second reactant.

In various embodiments of the present disclosure, the catalyst includes Ru, Rh, Pt, Pd or a combination thereof.

In various embodiments of the present disclosure, the catalyst is 0.1-1 part by weight based on 100 parts by weight of the second reactant.

In various embodiments of the present disclosure, hydrogenating the second reactant is under a pressure in a range of 500-1500 psi.

In various embodiments of the present disclosure, a reaction time of hydrogenating the second reactant is 0.5-6 hours.

In accordance with the method of manufacturing BHCD and derivatives thereof provided by the present disclosure, the first reactant derived from PET degradation can be directly hydrogenated under a lower temperature, compared with the conventional reaction temperature, without purification, in order to obtain BHCD having economic values. Therefore, PET can be simply and effectively recycled while using the method provided by the present disclosure.

BRIEF DESCRIPTION OF THE DRAWINGS

Aspects of the present disclosure are best understood from the following detailed description when read with the accompanying FIGURES. It is noted that, in accordance with the standard practice in the industry, various features are not drawn to scale. In fact, the dimensions of the various features may be arbitrarily increased or reduced for clarity of discussion.

FIG. 1 is a flow chart illustrating a method of manufacturing bis(2-hydroxyethyl) cyclohexane-1,4-dicarboxylate (BHCD) and derivatives thereof.

DETAILED DESCRIPTION OF THE PREFERRED EMBODIMENT

The following embodiments are disclosed with accompanying diagrams for detailed description. For illustration clarity, many details of practice are explained in the following descriptions. However, it should be understood that these details of practice do not intend to limit the present invention. That is, these details of practice are not necessary in parts of embodiments of the present invention. Furthermore, for simplifying the drawings, some of the conventional structures and elements are shown with schematic illustrations.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

In order to solve the issue met in the art, the present disclosure provides a method of manufacturing bis(2-hydroxyethyl) cyclohexane-1,4-dicarboxylate (BHCD) and derivatives thereof. According to the method of the present disclosure, a first reactant, which is derived from PET degradation and includes BHET monomer, BHET dimer and BHET oligomer, can be directly hydrogenated to obtain BHCD and the derivatives thereof without the purification before hydrogenation. Therefore, PET can be simply and effectively recycled while using the method provided by the present disclosure.

PET of the present disclosure may include, but not limited to, virgin PET, recycled PET, post consumer PET, PET precursor, etc.

BHCD manufactured by the present method is usually added in PET or polyurethane (PU) to effectively reduce the crystallization rate and improve the yellowing phenomenon. In addition, BHCD can be used as a synthetic precursor of cyclohexanedimethanol (CHDM), and CHDM is usually used as an additional monomer in polyester industry. CHDM can be used to synthesize the copolyesters such as poly1,4-cyclohexylene dimethylene terephthalate (PCT), polyethylene terephthalate glycol-modified (PETG), poly1,4-cyclohexylene dimethylene terephthalate glycol-modified (PCTG), etc., which have high thermal stability, good processability and high transparency.

BHCD derivatives of the present disclosure may include, but not limited to, a compound including a structure represented by formula (2):

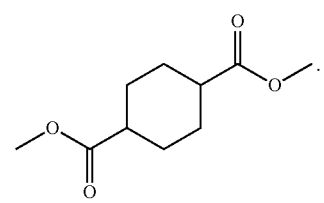

(2)

BHCD derivatives of the present disclosure may include, but not limited to, a compound including a structure represented by formula (3):

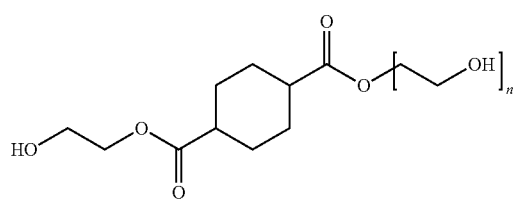

(3)

in which n is an integer of 1 to 10.

BHCD derivatives of the present disclosure may include, but not limited to, a compound including a structure represented by formula (4):

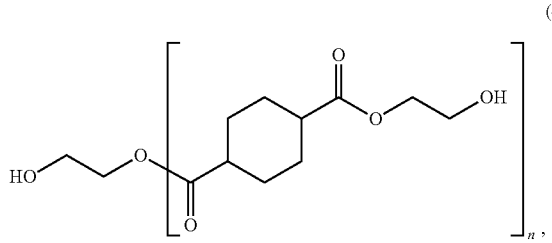

(4)

in which n is an integer of 1 to 10.

Specifically, the examples of BHCD derivatives of the present disclosure are bis(2-hydroxyethyl) cyclohexane-1,4-dicarboxylate, 1,4-cyclohexanedicarboxylic acid, 1,1'-(1,2-ethanediyl) 4,4'-bis(2-hydroxyethyl) ester and 1,4-cyclohexanedicarboxylic acid, 2-(2-hydroxyethoxy)ethyl 2-hydroxyethyl ester.

The present disclosure provides a method (100) of manufacturing bis(2-hydroxyethyl) cyclohexane-1,4-dicarboxylate (BHCD) and derivatives thereof. The method includes the following steps. A first reactant including bis-hydroxyethyl terephthalate (BHET) is provided (step 101). 2-(2-hydroxyethoxy)ethyl 2-hydroxyethyl terephthalate (BHEET) is added to the first reactant including BHET to form a second reactant (step 103). The second reactant is hydrogenated (step 105).

Please refer to FIG. 1. FIG. 1 is a flow chart illustrating a method (100) of manufacturing BHCD and derivatives thereof. Step 101 is providing a first reactant including BHET. The first reactant including BHET is derived by PET degradation, and the BHET in the first reactant may be existed as monomer, dimer, oligomer or a combination thereof.

Specifically, the first reactant may include BHET monomer and BHET dimer. In accordance with some embodiments, the BHET dimer is 0-100 parts by weight based on 100 parts by weight of the BHET monomer in the first reactant. Preferably, the BHET dimer is 0-80 parts by weight. More preferably, the BHET dimer is 0-60 parts by weight.

In some embodiments, BHET dimer is 1,4-Benzenedicarboxylic acid, 1,1'-(1,2-ethanediyl) 4,4'-bis (2-hydroxyethyl) ester.

In some embodiments, BHET oligomer has a structure represented by formula (1):

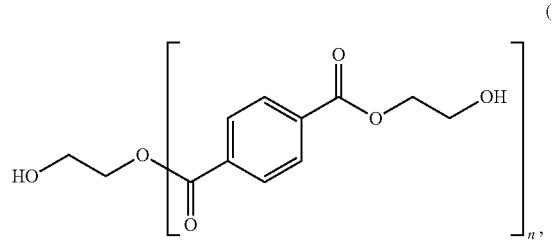

(1)

in which n is an integer of 3 to 10.

Continuing to refer to FIG. 1, step 103 is adding BHEET to the first reactant including BHET to form a second reactant. In the first reactant, the melting point of BHET monomer is at 110° C., and the melting point of BHET dimer is at a temperature in a range of 170-174° C. However, through adding BHEET to the first reactant, the subsequent hydrogenation of BHET monomer, BHET dimer and BHET oligomer in the second reactant can be performed at about or lower than the melting point of BHET monomer because of the presence of BHEET.

According to an embodiment, the BHEET is 0.5-100 parts by weight based on 100 parts by weight of the BHET monomer in the second reactant. Preferably, the BHEET is 7-60 parts by weight based. More preferably, the BHEET is 25-50 parts by weight. In some embodiments, the second reactant further includes BHET dimer, and the BHET dimer is 0-100 parts by weight based on 100 parts by weight of the BHET monomer in the second reactant. Preferably, the BHET dimer is 0-80 parts by weight. More preferably, the BHET dimer is 0-60 parts by weight.

Continuing to refer to FIG. 1, step 105 is that hydrogenating the second reactant. In some embodiments, the second reactant merely includes the first reactant and BHEET without solvent, so that hydrogenating the second reactant is under a solvent-free condition. According to some embodiments, hydrogenating the second reactant is at a temperature in a range of 80° C.-115° C. and a pressure in a range of 500-1500 psi for 0.5-6 hours. In accordance to another embodiment, hydrogenating the second reactant is at a temperature in a range of 85° C.-110° C. and a pressure in a range of 800-1200 psi.

In some embodiments, since the chemical structure of BHEET is similar to the structure of BHET, BHEET may not only promote the hydrogenation of BHET but also be hydrogenated to become valuable products during the hydrogenation process.

In some embodiments, the second reactant includes the monomer and dimer of BHET as well as BHEET. BHCD, 1,4-cyclohexanedicarboxylic acid, 1,1'-(1,2-ethanediyl) 4,4'-bis(2-hydroxyethyl) ester) and 1,4-cyclohexanedicarboxylic acid, 2-(2-hydroxyethoxy)ethyl 2-hydroxyethyl ester are respectively produced by hydrogenating the monomer and dimer of BHET as well as BHEET of the second reactant. 1,4-cyclohexanedicarboxylic acid, 1,1'-(1,2-ethanediyl) 4,4'-bis(2-hydroxyethyl) ester) and 1,4-cyclohexanedicarboxylic acid, 2-(2-hydroxyethoxy)ethyl 2-hydroxyethyl ester as well as BHCD have the same applicability and economic value.

In some embodiments, the method of the present disclosure further includes adding a catalyst to the second reactant before hydrogenating the second reactant. For instance, the catalyst includes Ru, Rh, Pt, Pd or a combination thereof.

The catalyst is important during the hydrogenation process. However, it should be noted that just adding more than a certain amount of the catalyst can get a good effect of hydrogenating. In an embodiment, the catalyst is 0.1-1.0 part by weight based on 100 parts by weight of the second reactant. In another embodiment, the catalyst is 0.25-0.75 part by weight based on 100 parts by weight of the second reactant. In further embodiment, the catalyst is 0.4-0.6 part by weight based on 100 parts by weight of the second reactant. Preferably, the catalyst is 0.5 part by weight.

Given the above, the method of manufacturing BHCD and the derivatives thereof provided by the present disclosure may hydrogenating the second reactant, which includes BHEET as well as BHET monomer, BHET dimer, BHET oligomer or a combination thereof, at about or lower than the melting point of BHET monomer in a solvent-free condition through adding BHEET, and may also omit the purification step before hydrogenating.

Two following embodiments of the present disclosure more clearly described the actual ratio of the components in a reactant (experimental groups 1-10) of hydrogenation step and a hydrogenation conversion rate of benzene after hydrogenating. The following embodiments are only exemplary, but not intended to limit the present disclosure. One person skilled in the art may elastically select the appropriate ratio of the components in a reactant and kinds of catalyst according to the actual needs. The calculation method of benzene hydrogenation conversion rate used nuclear magnetic resonance (NMR) spectroscopy to analyze the integrated area ratio of disappeared signal of benzene in the product. Dimethyl sulfoxide (DMSO) was used as a solvent. The portion which the chemical shifted about 8.1 ppm was a signal of benzene, and another portion which the chemical shifted about 1.3-1.9 ppm was a signal of cyclohexane. Compared the signal integrated area of two portions to speculate the benzene hydrogenation conversion rate.

Manufacturing a Reactant

First, 300 g of PET polyester pellets were added into 1500 g of ethylene glycol (EG), and then 3 g of zinc acetate catalyst was added as well as the temperature was raised to 190-200° C. to reflux and react for 3 hours. Next, the mixture is allowed to stand for cooling until reaching room temperature, and suction filtered to separate a crude solid product. BHET monomer and BHET dimer may be respectively purified from the crude product by re-crystallizing.

Manufacturing BHEET 10 g of BHET was added to a flask with 100 mL, and then 11.4 mL of diethylene glycol (DEG) as well as 7.4 mg of zinc acetate were added. After reacting for 6 hours at 180° C., the flask was moved to room temperature. The extraction is performed by ethyl acetate (EtOAc) and water to remove ethylene glycol (EG) and DEG. The organic layer was collected and concentrated, and then purified by column chromatography (the ratio of eluent was EtOAc:n-Hexane=3:1). Finally, recrystallization was performed by water and ethanol to remove solid impurities, and then concentration was performed to obtain BHEET.

Embodiment 1

Experimental groups 1-5 included 20 g of reactant and 0.1 g of Ru catalyst (equal to 2 g of Ru/C catalyst). The reactant included BHET monomer and BHEET. Based on 100 parts by weight of BHET monomer, different amounts of BHEET were added as shown in Table 1. Ru/C catalyst used carbon as a carrier, and had 5 wt % of active metal, Ru. First, the reactant and Ru/C catalyst were hydrogenated at different temperature and a pressure of 800 psi for 3 hours. Subsequently, the benzene hydrogenation conversion rate, which may represent as the product rate of BHET monomer and BHEET after hydrogenating, was speculated by above method, and the results shown in Table 1.

TABLE 1

|  | Experimental group 1 | Experimental group 2 | Experimental group 3 | Experimental group 4 | Experimental group 5 |
|---|---|---|---|---|---|
| Amounts of BHET monomer in the reactant | 18.60 g (100 parts by weight) | 19.00 g (100 parts by weight) | 19.30 g (100 parts by weight) | 20.00 g (100 parts by weight) | 20.00 g (100 parts by weight) |
| Amounts of BHEET in the reactant | 1.40 g (7.5 parts by weight) | 1.00 g (5.2 parts by weight) | 0.70 g (3.6 parts by weight) | 0.00 g | 0.00 g |
| Temperature (° C.) | 100 | 100 | 100 | 100 | 160 |
| Pressure (psi) | 800 | 800 | 800 | 800 | 800 |
| Benzene hydrogenation conversion rate | >99% | 95% | 27% | 0% | >99% |

Please refer to Table 1. Comparing experiment groups 1-3 and experiment group 4, it can be seen that when the reactant was in the absence of BHEET (experimental group 4), the benzene hydrogenation conversion rate of the reactant is 0% at the same temperature (100° C.) and pressure (800 psi). In other words, no product was produced by hydrogenating BHET monomer and BHEET. However, when the reactant was in the presence of BHEET, the reactant may be hydrogenated at a temperature (e.g. 100° C.) lower than the melting point of BHET monomer. Besides, the benzene hydrogenation conversion rate was increased when the amount of BHEET was increased. In accordance with Table 1, when amount of BHEET was 5.2 parts by weight (experimental group 2), the benzene hydrogenation conversion rate of the reactant can meet 95%. When amount of BHEET was 7.5 parts by weight (experimental group 1), the reactant had a better benzene hydrogenation conversion rate, >99%.

Continue to refer to Table 1. Comparing experimental group 4 and experimental group 5, it can be seen that when the reactant was in the absence of BHEET, the benzene hydrogenation conversion rate of the reactant is 0% at a temperature (e.g. 100° C.) lower than the melting point of the reactant. The temperature had to be increased to 160° C., so that the benzene hydrogenation conversion rate of the reactant may be increased to >99%.

Given the above, when the reactant was in the absence of BHEET, BHET may be converted to BHCD by hydrogenation process at 160° C. However, when the reactant was in the presence of BHEET, BHET may be converted to BHCD by hydrogenation process at 100° C. Therefore, the reaction temperature of hydrogenation process may be decreased to reduce loss of energy because of the presence of BHEET in the reactant.

Embodiment 2

Experimental groups 6-10 included 20 g of reactant and 0.1 g of Ru catalyst (equal to 2 g of Ru/C catalyst). The reactant included BHET monomer, BHET dimer and BHEET. Based on 100 parts by weight of BHET monomer, different amounts of BHET dimer and BHEET were added as shown in Table 2. Ru/C catalyst used carbon as a carrier, and had 5 wt % of active metal, Ru. First, the reactant and Ru/C catalyst were hydrogenated at a temperature of 100° C. and a pressure of 800 psi for 3 hours. Subsequently, the benzene hydrogenation conversion rate, which may represent as the product rate of BHET monomer, BHET dimer and BHEET after hydrogenating, was speculated by above method, and the results shown in Table 2.

TABLE 2

|  | Experimental group 6 | Experimental group 7 | Experimental group 8 | Experimental group 9 | Experimental group 10 |
| --- | --- | --- | --- | --- | --- |
| Amounts of BHET monomer in the reactant | 10.00 g (100 parts by weight) | 10.61 g (100 parts by weight) | 11.25 g (100 parts by weight) | 11.86 g (100 parts by weight) | 12.50 g (100 parts by weight) |
| Amounts of BHET dimer in the reactant | 6.00 g (60 parts by weight) | 6.38 g (60 parts by weight) | 6.75 g (60 parts by weight) | 7.14 g (60 parts by weight) | 7.50 g (60 parts by weight) |
| Amounts of BHEET in the reactant | 4.00 g (40 parts by weight) | 3.00 g (28 parts by weight) | 2.00 g (18 parts by weight) | 1.00 g (8.4 parts by weight) | 0.00 g |
| Temperature (° C.) | 100 | 100 | 100 | 100 | 100 |
| Pressure (psi) | 800 | 800 | 800 | 800 | 800 |
| Benzene hydrogenation conversion rate | >99% | >99% | 45% | 40% | 0% |

In the conventional method, since a product obtained by PET degradation usually includes BHET monomer and BHET dimer, the product has to be purified to obtain BHET monomer before hydrogenation process in order to produce BHCD. However, the present disclosure may omit the purification step, and directly hydrogenate the product, which is obtained by PET degradation and includes BHET monomer and BHET dimer. In addition, the present disclosure has a high benzene hydrogenation conversion rate.

Please refer to Table 2. The amounts of BHET monomer and BHET dimer in the reactant of the experimental groups 6-10 simulated proper ratios of components in the reactant after PET degradation. Comparing experiment groups 6-9 and experiment group 10, it can be seen that when the reactant was in the absence of BHEET (experimental group 10), the benzene hydrogenation conversion rate of the reactant is 0% at the same temperature (100° C.) and pressure (800 psi). In other words, no product was produced by hydrogenating BHET monomer and BHET dimer.

However, when the reactant was in the presence of BHEET, the reactant may be hydrogenated at a temperature (e.g. 100° C.) lower than the melting point of BHET monomer. Besides, the benzene hydrogenation conversion rate was increased when the amount of BHEET was increased. In accordance with Table 2, when amount of BHEET was more than 28 parts by weight (experimental groups 7 and 6), the benzene hydrogenation conversion rate of the reactant can meet >99%.

Given the above, although the reactant was in the presence of BHET dimer, BHCD and 1,4-cyclohexanedicarboxylic acid, 1,1'-(1,2-ethanediyl) 4,4'-bis(2-hydroxyethyl) ester still can be respectively produced by hydrogenating BHET monomer and BHET dimer at 100° C. and 800 psi with a high benzene hydrogenation conversion rate while using the method provided by the present disclosure.

Please simultaneously refer to Table 1 and Table 2. It should be noted that if there was BHET dimer in the reactant, BHCD and 1,4-cyclohexanedicarboxylic acid, 1,1'-(1,2-ethanediyl) 4,4'-bis(2-hydroxyethyl) ester still can be respectively produced by hydrogenating BHET monomer and BHET dimer at 100° C. and 800 psi after adding more amount of BHEET in the reactant. Accordingly, it can prove that the present disclosure may omit the purification step after PET degradation, directly hydrogenate the product obtained by PET degradation, and have a high hydrogenation conversion rate.

In accordance with above embodiments of the present disclosure, the method of manufacturing BHCD and the derivatives thereof provided by the present disclosure may omit the purification step before hydrogenation, and directly hydrogenated the product obtained by PET degradation in order to obtain BHCD having economic values. Therefore, PET can be simply and effectively recycled while using the method provided by the present disclosure. In addition, through adding BHEET to the reactant, the reactant including BHET monomer, BHET dimer, BHET oligomer or a combination thereof may be hydrogenated at about or lower than the melting point in the solvent-free condition with a high benzene hydrogenation conversion rate while using the method of manufacturing BHCD and the derivatives thereof provided by the present.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of manufacturing bis(2-hydroxyethyl) cyclohexane-1,4-dicarboxylate (BHCD) and derivatives thereof, the method comprising:
   providing a first reactant comprising bis-hydroxyethyl terephthalate (BHET);
   adding 2-(2-hydroxyethoxy)ethyl 2-hydroxyethyl terephthalate (BHEET) to the first reactant comprising BHET to form a second reactant; and
   hydrogenating the second reactant.

2. The method of claim 1, wherein the BHET in the first reactant is existed as monomer, dimer, oligomer or a combination thereof.

3. The method of claim 2, wherein the BHET dimer is 0-100 parts by weight based on 100 parts by weight of the BHET monomer in the first reactant.

4. The method of claim 2, wherein the BHET dimer is 0-80 parts by weight based on 100 parts by weight of the BHET monomer in the first reactant.

5. The method of claim 2, wherein the BHET dimer is 0-60 parts by weight based on 100 parts by weight of the BHET monomer in the first reactant.

6. The method of claim 2, wherein the BHET oligomer has a structure represented by formula (1):

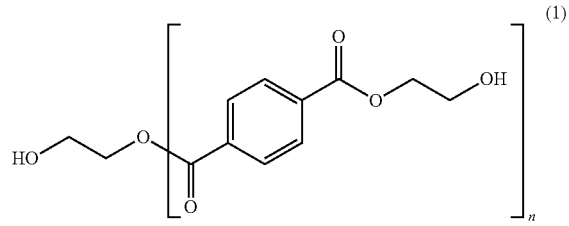

wherein n is an integer of 3 to 10.

7. The method of claim 1, wherein hydrogenating the second reactant is under a solvent-free condition.

8. The method of claim 1, wherein hydrogenating the second reactant is at a temperature in a range of 80° C.-115° C.

9. The method of claim 1, wherein hydrogenating the second reactant is at a temperature in a range of 85° C.-110° C.

10. The method of claim 1, wherein the BHEET is 0.5-100 parts by weight based on 100 parts by weight of the BHET monomer in the second reactant.

11. The method of claim 1, wherein the BHEET is 7-60 parts by weight based on 100 parts by weight of the BHET monomer in the second reactant.

12. The method of claim 1, wherein the BHEET is 25-50 parts by weight based on 100 parts by weight of the BHET monomer in the second reactant.

13. The method of claim 1, further comprising:
    adding a catalyst to the second reactant before hydrogenating the second reactant.

14. The method of claim 13, wherein the catalyst comprises Ru, Rh, Pt, Pd or a combination thereof.

15. The method of claim 13, wherein the catalyst is 0.1-1.0 part by weight based on 100 parts by weight of the second reactant.

16. The method of claim 1, wherein hydrogenating the second reactant is under a pressure in a range of 500-1500 psi.

17. The method of claim 1, wherein a reaction time of hydrogenating the second reactant is 0.5-6 hours.

* * * * *